United States Patent
Tsuyuki et al.

(10) Patent No.: US 7,668,286 B2
(45) Date of Patent: Feb. 23, 2010

(54) X-RAY CT APPARATUS

(75) Inventors: Masaharu Tsuyuki, Tochigi (JP);
Shinsuke Tsukagoshi, Tochigi (JP)

(73) Assignees: Kabushiki Kaisha Toshiba, Tokyo (JP);
Toshiba Medical Systems Corporation, Otawara-Shi (JP)

( * ) Notice: Subject to any disclaimer, the term of this patent is extended or adjusted under 35 U.S.C. 154(b) by 0 days.

(21) Appl. No.: 12/200,065

(22) Filed: Aug. 28, 2008

(65) Prior Publication Data

US 2009/0060125 A1 Mar. 5, 2009

(30) Foreign Application Priority Data

Sep. 3, 2007 (JP) ............... 2007-228062

(51) Int. Cl.
*A61B 6/00* (2006.01)
(52) U.S. Cl. ............................. 378/8; 378/16
(58) Field of Classification Search ............ 378/4, 378/8, 5, 16
See application file for complete search history.

(56) References Cited

U.S. PATENT DOCUMENTS

2006/0013358 A1* 1/2006 Seto et al. ............... 378/16
2007/0053483 A1 3/2007 Nagata et al.

FOREIGN PATENT DOCUMENTS

| JP | 2004-208715 | 7/2004 |
| JP | 2006-20708 | 1/2006 |
| JP | 2007-117719 | 5/2007 |

* cited by examiner

*Primary Examiner*—Hoon Song
(74) *Attorney, Agent, or Firm*—Oblon, Spivak, McClelland, Maier & Neustadt, L.L.P.

(57) ABSTRACT

An X-ray CT apparatus sets at least an imaging-subject area to be imaged, and a heart imaging area included in the imaging-subject area and determined based on a position and size of a heart on a subject P. When an image is taken, the X-ray CT apparatus sets imaging conditions, such as whether electrocardiographic synchronization is required for imaging and a type of reconstruction mode, based on each set imaging area.

9 Claims, 6 Drawing Sheets

X-RAY CT APPARATUS

CROSS-REFERENCE TO RELATED APPLICATIONS

This application is based upon and claims the benefit of priority from the prior Japanese Patent Application No. 2007-228062, filed on Sep. 3, 2007; the entire contents of which are incorporated herein by reference.

BACKGROUND OF THE INVENTION

1. Field of the Invention

The present invention relates to an X-ray computed tomography (CT) apparatus that takes an image of a subject by irradiating the subject with X-rays, collecting projection data, and reconstructing an image from the collected projection data. In particular, the present invention relates to an imaging condition setting method used when a wide area including a heart is imaged.

2. Description of the Related Art

Conventionally, an X-ray CT apparatus irradiates a subject with X-rays and collects projection data by detecting the X-rays passing through the subject. The X-ray CT apparatus then reconstructs an image from the collected projection data. In recent years, heart examinations have generally been performed using the X-ray CT apparatus. When the X-ray CT apparatus takes an image of a heart, a method is used in which imaging is performed synchronously with a cardiac cycle of the heart. The method is referred to as "electrocardiographic synchronized imaging" (refer to, for example, JP-A 2007-117719 (KOKAI)).

On the other hand, an imaging method referred to as "step-and-shoot" is also used by the X-ray CT apparatus. In "step-and-shoot", a portion of the subject is irradiated with the X-rays and the irradiated portion is then imaged. Subsequently, while irradiation with the X-rays is stopped, the subject and a top plate on which the subject is placed are moved in a body axis direction by a predetermined distance. Another portion of the subject is irradiated with the X-rays and the irradiated portion is then imaged. Movement and imaging are repeated, allowing a wide area of the subject to be imaged.

When a wide area including a heart is imaged using the X-ray CT apparatus, imaging is performed by a combination of electrocardiographic synchronized imaging and "step-and-shoot".

In the above-described electrocardiographic synchronized imaging, imaging is timed to be synchronous with the cardiac cycle. Therefore, wait times occur in correspondence with the cardiac cycle. In actuality, imaging is performed every one to two heartbeats. Therefore, electrocardiographic synchronized imaging is time-consuming compared to ordinary imaging (imaging that is not synchronized with the cardiac cycle).

The heart is an organ that constantly repeats contraction and expansion with each heartbeat. However, for example, an examination of a fine organ, such as a coronary artery, requires a clear image that is little affected by movement. To obtain an image that is little affected by movement, improvement is required in a temporal resolution of the image reconstructed from the projection data. Reconstruction methods that improve the temporal resolution are, for example, half reconstruction and segment reconstruction. In a half reconstruction operation, the image is reconstructed using projection data collected while an X-ray tube is rotating within a range of 180 degrees plus $\alpha$ ($\alpha$ being a fan angle). Compared to when the image is reconstructed using 360-degree range projection data (full reconstruction), the half reconstruction can shorten the temporal resolution by approximately one-half.

On the other hand, in a segment reconstruction operation, pieces of projection data of a same cross-section and a same phase are extracted from pieces of projection data of a predetermined number of heartbeats. The extracted pieces of projection data are combined to form a piece of projection data of a range of 180 degrees plus $\alpha$. Subsequently, the half reconstruction operation is performed. Compared to when the image is reconstructed using the 360 degree range projection data, the segment reconstruction can shorten the temporal resolution to about $(180+\alpha)/n$ when an n number of heartbeats are used.

In this way, segment reconstruction can further improve the temporal resolution of the image, compared to half reconstruction. However, because the pieces of projection data of a plurality of heartbeats are required, imaging in segment reconstruction mode is more time-consuming than that in half reconstruction mode. Therefore, an extremely long imaging time is conventionally required to image the wide area including the heart by the combination of electrocardiographic synchronized imaging and "step-and-shoot", and to obtain an image with high temporal resolution.

However, even when the wide area including the heart is imaged, in actuality, some regions are not required to be imaged by electrocardiographic synchronized imaging while other regions do not require an image with high temporal resolution. Specifically, a region that does not move because of being far from the heart is not required to be imaged by electrocardiographic synchronized imaging. A region that moves because of being near the heart, but has less movement than the heart, does not require an image with high temporal resolution.

Therefore, in imaging combining electrocardiographic synchronized imaging and "step-and-shoot", optimal imaging conditions related to electrocardiographic synchronization and reconstruction modes are required to be set depending on the region to optimize the time required for a series of imaging operations. Conventionally, imaging conditions have been manually set by an operator, thus requiring a significant amount of work. Therefore, in the imaging combining the electrocardiographic synchronized imaging and "step-and-shoot", how to automatically set the optimal imaging conditions for each region and shorten the time required for an overall imaging operation is an important issue.

SUMMARY OF THE INVENTION

According to one aspect of the present invention, an X-ray CT apparatus includes a top plate moving unit that stepwisely moves a top plate on which a subject is placed in a body axis direction; a rotation mechanism unit that rotates an X-ray irradiating unit on a circular orbit approximately centering on the subject for every time the top plate moving unit moves the top plate; a data collecting unit that collects projection data obtained by detecting X-rays passing through the subject; an image reconstructing unit that reconstructs an image from the projection data collected by the data collecting unit; and a first imaging-area setting unit that sets, on the subject, a first imaging area including a first imaging region that moves cyclically or non-cyclically, and a second imaging area including a second imaging region having less movement than the first imaging region, wherein the image reconstruction unit reconstructs the image synchronously with movements of the first imaging region when the top plate moving unit moves the top plate to a position at which the first imaging area is irradiated with the X-rays, and reconstructs the image without synchronizing with movements of the second imaging region when the top plate moving unit moves the top plate to a position at which the second imaging area is irradiated with the X-rays.

DETAILED DESCRIPTION OF THE INVENTION

Exemplary embodiments of an X-ray CT apparatus according to the present invention are below described with reference to the attached drawings. An X-ray CT apparatus described herein can take an image of various regions on a subject in the same manner as a common X-ray CT apparatus. However, when the X-ray CT apparatus combines electrocardiographic synchronized imaging and "step-and-shoot" to image a wide area including a heart will mainly be described.

Figure 1:
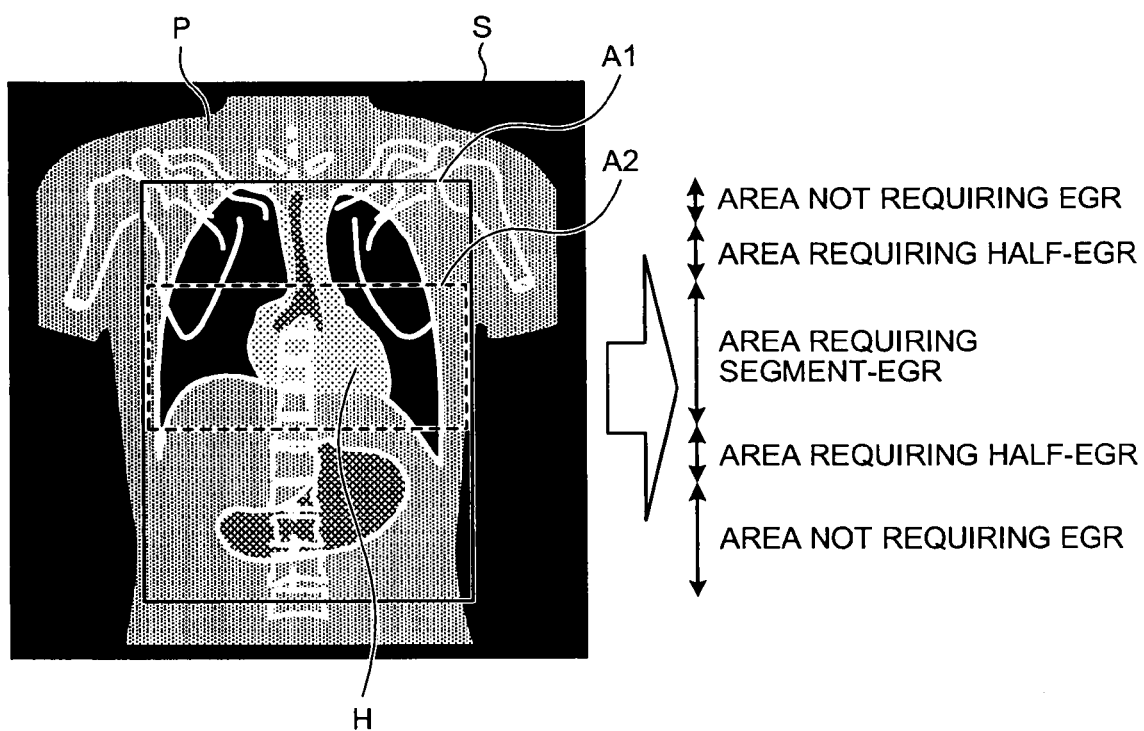
FIG. 1 is an explanatory diagram explaining a concept of an imaging condition setting method used by an X-ray CT apparatus according to a first embodiment.

First, a concept of an imaging condition setting method used by an X-ray CT apparatus according to a first embodiment will be described. FIG. 1 is an explanatory diagram explaining the concept of the imaging condition setting method used by the X-ray CT apparatus according to the first embodiment. The X-ray CT apparatus performs imaging by combining electrocardiographic synchronized imaging and "step-and-shoot" to image a wide area including a heart.

On the subject P, The X-ray CT apparatus sets at least an imaging-subject area to be imaged and a region imaging area on a subject P. The region imaging area is included within the imaging-subject area and determined depending on each region. When the X-ray CT apparatus takes an image, the x-ray CT apparatus sets imaging conditions for imaging based on each of the set imaging areas.

Specifically, the X-ray CT apparatus first displays a scanogram S (image used to set an imaging area) in which the subject P is imaged. The X-ray CT apparatus also displays frames A1 and A2, as shown in FIG. 1, used to receive a designation of an imaging area from an operator on the scanogram S. A frame A1 is used to receive a designation of the "imaging-subject area" indicating all areas to be imaged. A frame A2 is used to receive a designation of a "heart imaging area" within the imaging-subject area and including a heart H. The heart imaging area is determined based on a position and size of the heart H. Regions within the heart imaging area and its periphery move as a result of heartbeats and, therefore, are required to be imaged by electrocardiographic synchronized imaging. The operator can set an imaging-subject area and a heart imaging area to an arbitrary size and in an arbitrary position by moving the frames A1 and A2 over the scanogram S, and enlarging and shrinking the frames A1 and A2.

When each imaging-subject area is designated by the operator, the X-ray CT apparatus sets the heart imaging area (an area surrounded by the frame A2) as a "segment reconstruction area", sets an area that is the heart imaging area widened vertically by a predetermined length from which the heart imaging area is excluded as a "half reconstruction area", and sets the imaging-subject area (an area surrounded by the frame A1) from which the segment reconstruction area and the half reconstruction area are excluded as a "no-electrocardiographic synchronization area". The X-ray CT apparatus calculates a position and size of each area. The X-ray CT apparatus also stores the calculated results as imaging area information.

Then, when an instruction to start imaging is received from the operator, the X-ray CT apparatus moves a top plate in a body axis direction and performs a first imaging operation. At this time, the X-ray CT apparatus references the stored imaging area information and confirms a type of area in which an imaging position is included.

When the imaging position is included within the segment reconstruction area, the X-ray CT apparatus collects projection data while modulating the X-rays synchronously with electrocardiographic waveforms by irradiating the subject P with strong X-rays at an electrocardiographic phase range specified by the operator and irradiating the subject P with weak X-rays (or stopping irradiation) at other electrocardiographic phase ranges. The X-ray CT apparatus then reconstructs an image from the collected projection data using segment reconstruction. As a result, an image having a high temporal resolution can be obtained for an area including the heart H, namely an area having a large amount of movement in the region.

When the imaging position is included within the half reconstruction area, the X-ray CT apparatus collects projection data while modulating the X-rays synchronously with electrocardiographic waveforms by irradiating the subject P with strong X-rays at an electrocardiographic phase range specified by the operator and irradiating the subject P with weak X-rays (or stopping irradiation) at other electrocardiographic phase ranges. The X-ray CT apparatus then reconstructs an image from the collected projection data using half reconstruction. As a result, an image having a moderate temporal resolution can be obtained in an area surrounding the heart H, namely an area having a small amount of movement in the region. The image can be obtained in a shorter amount of time than through segment reconstruction.

When the imaging position is included within the no-electrocardiographic synchronization area, the X-ray CT apparatus collects projection data immediately after the top plate stops moving by irradiating the subject P with X-rays of a constant strength without modulating the X-rays synchronously with the electrocardiographic waveforms. The X-ray CT apparatus then reconstructs an image from the collected projection data using half reconstruction. As a result, an image can be obtained in a short amount of time without time-consuming electrocardiographic synchronized imaging being performed in an area far from the heart H, namely an area without movement in the region Then, after any of the imaging operations is performed, the X-ray CT apparatus moves the top plate in the body axis direction by a predetermined distance and performs a next imaging operation. The X-ray CT apparatus repeats movement of the top plate and imaging until an instruction to complete imaging is received from the operator.

Based on characteristics such as those above, in the X-ray CT apparatus according to the first embodiment, when the wide area including the heart is imaged, optimal imaging conditions (such as whether to perform electrocardiographic synchronization and type of reconstruction mode) are automatically set for each region, and time required for an overall imaging operation can be shortened.

Figure 2:
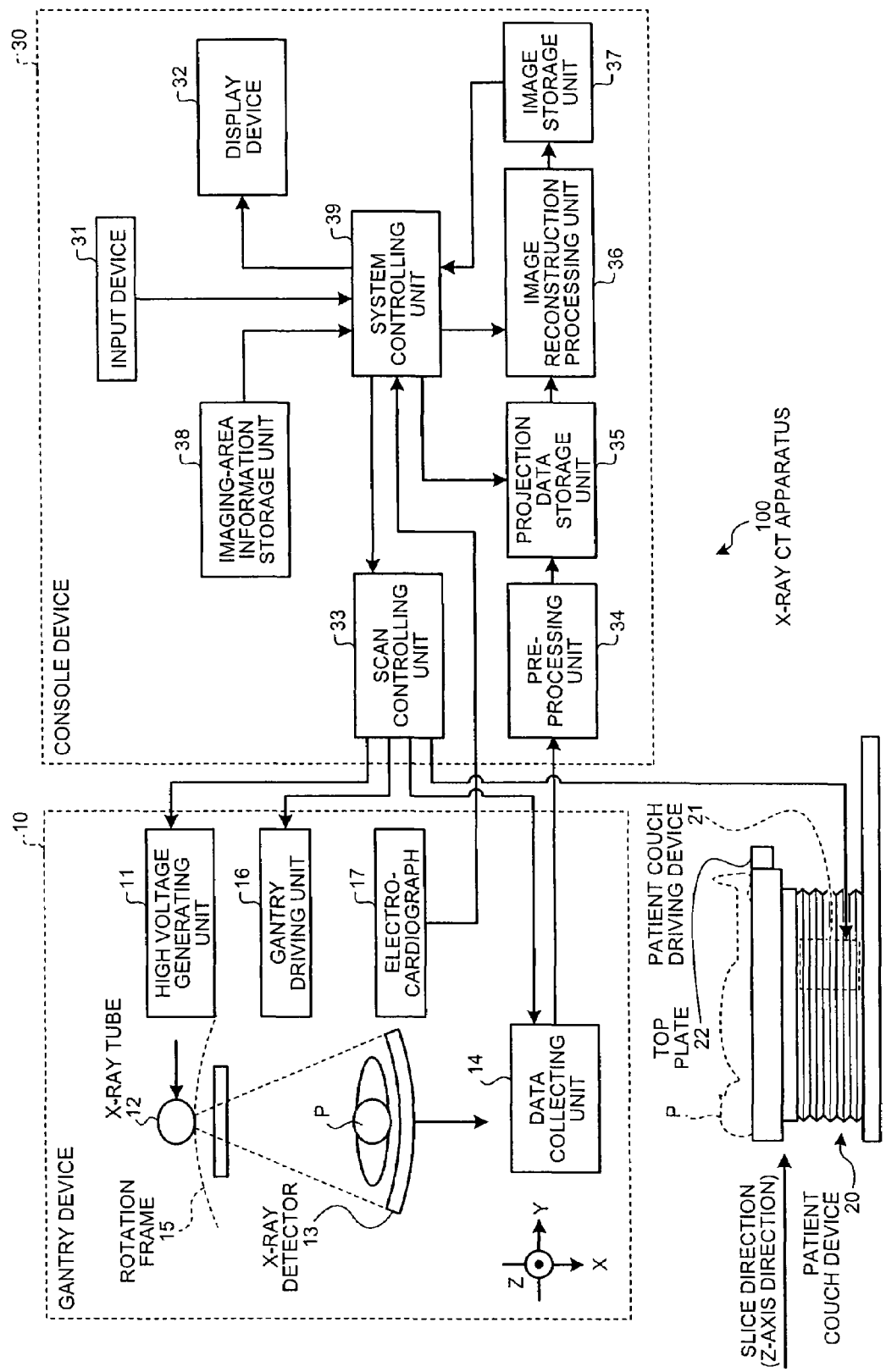
FIG. 2 is a functional block diagram of a configuration of the X-ray CT apparatus according to the first embodiment.

Next, a configuration of the X-ray CT apparatus according to the first embodiment will be described. FIG. 2 is a functional block diagram of a configuration of the X-ray CT apparatus according to the first embodiment. As shown in FIG. 2, an X-ray CT apparatus 100 includes a gantry device 10, a patient couch device 20, and a console device 30.

The gantry device 10 irradiates a subject P with X-rays and collects projection data. The gantry device 10 includes a high voltage generating unit 11, an X-ray tube 12, an X-ray detector 13, a data collecting unit 14, a rotation frame 15, a gantry driving unit 16, and an electrocardiograph 17.

The high voltage generating unit 11 supplies the X-ray tube 12 with a high voltage. The X-ray tube 12 is a vacuum tube that generates the X-rays using the high voltage supplied from the high voltage generating unit 11. The X-ray detector 13 detects the X-rays passing through the subject P. The data collecting unit 14 generates the projection data using the X-rays detected by the X-ray detector 13.

The rotation frame 15 is a ring-shaped frame continuously rotating at a high speed. The rotation frame 15 holds the X-ray tube 12 and the X-ray detector 13 so that the X-ray tube 12 and the X-ray detector 13 face each other with the subject P therebetween. The gantry driving unit 16 rotatably drives the rotation frame 15, thereby revolving the X-ray tube 12 and the X-ray detector 13 on a circular orbit centering on the subject P. The electrocardiograph 17 detects a weak current generated from the subject P's heart by an electrode attached to the subject P. The electrocardiograph 17 then outputs an electrocardiographic signal based on the detected current.

The subject P is placed on the patient couch device 20. The patient couch device 20 includes a top plate 22 and a patient couch driving device 21. The subject P is placed on the top plate 22 when imaging is performed. The patient couch driving device 21 moves the top plate 22 in a slice direction.

The console device 30 receives operation input by an operator to drive the X-ray CT apparatus 100. The console device 30 also reconstructs an image from the projection data collected by the gantry device 10. The console device 30 includes an input device 31, a display device 32, a scan controlling unit 33, a pre-processing unit 34, an projection data storage unit 35, an image reconstruction processing unit 36, an image storage unit 37, an imaging-area information storage unit 38, and a system controlling unit 39.

The input device 31 is a mouse, a keyboard, and the like used by the operator to enter instructions for the X-ray CT apparatus 100. The display device 32 displays an image stored in the image storage unit and a screen for receiving various instructions from the operator described hereinafter and the like.

The scan controlling unit 33 is a processing unit that irradiates the subject P's heart with the X-rays and collects the projection data by driving the high voltage generating unit 11, the data collecting unit 14, the gantry driving unit 16, and the patient couch driving device 21 based on imaging conditions specified by the system controlling unit 39, under control of the system controlling unit 39 described hereinafter.

The pre-processing unit 34 is a processing unit that performs pre-processing, such as sensitivity correction, of the projection data generated by the data collecting unit 14. The projection data storage unit 35 stores the projection data pre-processed by the pre-processing unit 34.

The image reconstruction processing unit 36 reconstructs the image from the projection data stored in the projection data storage unit 35, under control of the system controlling unit 39. The image reconstruction processing unit 36 provides a function for reconstructing the image using at least half reconstruction and segment reconstruction. The image reconstruction processing unit 36 changes a reconstruction mode between the half reconstruction and the segment reconstruction, corresponding to the instructions from the system controlling unit 39. It is assumed that a number of heartbeats used when the image is reconstructed using segment reconstruction is set in advance by the operator.

The image storage unit 37 stores the image reconstructed by the image reconstruction processing unit 36. The imaging-area information storage unit 38 stores the imaging area information indicating the position and size of an imaging area received by the system controlling unit 39 described hereafter from the operator.

The system controlling unit 39 controls operations performed by the gantry device 10, the patient couch device 20, and the console device 30, thereby controlling the overall X-ray CT apparatus. For example, when imaging combining electrocardiographic synchronized imaging and "step-and-shoot" is performed, the system controlling unit 39 first displays the scanogram S in which the subject P is imaged in the display device 32. The system controlling unit 39 also displays the frame A1 used to designate the imaging-subject area indicating an overall area to be imaged and the frame A2 used to designate the heart imaging area within the imaging-subject area that requires electrocardiographic synchronized imaging, as shown in FIG. 1. The system controlling unit 39 then receives designation of the imaging-subject area and the heart imaging area from the operator.

Then, when the operator designates each imaging-subject area, the system controlling unit 39 sets the heart imaging area (the area surrounded by the frame A2) as the "segment reconstruction area", sets the area that is the heart imaging area widened vertically by a predetermined length (for example, an area respectively widened by 50 millimeters in an upward direction and a downward direction) from which the heart imaging area is excluded as the "half reconstruction area", and sets the imaging-subject area (the area surrounded by the frame A1) from which the segment reconstruction area and the half reconstruction area are excluded as the "no-electrocardiographic synchronization area". The system controlling unit 39 calculates the position and size of each area. The system controlling unit 39 also stores the calculated results in the imaging-area information storage unit 38 as the imaging area information.

Then, when the instruction to start imaging is received from the operator, the system controlling unit 39 controls the scan controlling unit 33 to move the top plate 22 in the body axis direction and perform a first imaging operation. At this time, the system controlling unit 39 references the imaging area information stored in the imaging-area information storage unit 38 and confirms the type of area in which the imaging position is included. The system controlling unit 39 performs imaging and image reconstruction based on the confirmed type of area.

When the imaging position is included within the segment reconstruction area, the system controlling unit 39 controls the scan controlling unit 33 based on an electrocardiographic signal outputted from the electrocardiograph 17 to collect the projection data while modulating the X-rays synchronously with the electrocardiographic waveforms by irradiating the subject P with strong X-rays at an electrocardiographic phase range specified by the operator and irradiating the subject P with weak X-rays (or stopping irradiation) at other electrocardiographic phase ranges. The system controlling unit 39 also controls the image reconstruction processing unit 36 to reconstruct an image from the collected projection data using segment reconstruction. At this time, the system controlling unit 39 instructs to the scan controlling unit 33 imaging conditions in which a rotation speed of the rotation frame 15 and an imaging time are set such that temporal resolution is an optimal value.

When the imaging position is included within the half reconstruction area, the system controlling unit 39 controls the scan controlling unit 33 based on an electrocardiographic signal outputted from the electrocardiograph 17 to collect the projection data while modulating the X-rays synchronously with electrocardiographic waveforms by irradiating the subject P with strong X-rays at an electrocardiographic phase range specified by the operator and irradiating the subject P with weak X-rays (or stopping irradiation) at other electrocardiographic phase ranges. The system controlling unit 39 also controls the image reconstruction processing unit 36 to reconstruct an image from the collected projection data using half reconstruction. At this time, the system controlling unit 39 instructs to the scan controlling unit 33 imaging conditions in which the rotation speed of the rotation frame 15 is at a maximum.

When the imaging position is included within the no-electrocardiographic synchronization area, the system controlling unit 39 controls the scan controlling unit 33 immediately after the top plate 22 stops moving to collect projection data by irradiating the subject P with X-rays of a constant strength without modulating the X-rays synchronously with the electrocardiographic waveforms. The system controlling unit 39 also controls the image reconstruction processing unit 36 to reconstruct an image from the collected projection data using half reconstruction. At this time, the system controlling unit 39 instructs to the scan controlling unit 33 imaging conditions in which the rotation speed of the rotation frame 15 is a speed specified by the operator in advance.

Here, the system controlling unit 39 instructs to the scan controlling unit 33 the imaging conditions in which the rotation speed of the rotation frame 15 is maximum when the half reconstruction area is imaged, and the imaging conditions in which the rotation speed of the rotation frame 15 is a speed specified by the operator in advance when the no-electrocardiographic synchronization area is imaged. However, for example, the system controlling unit 39 can instruct imaging conditions in which the rotation speed of the rotation frame 15 is the same as that when the segment reconstruction area is imaged for all areas.

As a result, the rotation speed of the rotation frame 15 is the same regardless of the area being imaged. Because a rotation mechanism of the gantry device 10 including the rotation frame 15 and the like is generally heavy, changing the rotation speed takes time. In such instances, an overall imaging time becomes shorter when rotation speeds are the same, compared to when the rotation speed is changed for each area, because a wait time required for adjustment of the rotation speed is omitted.

Here, when the imaging position is included within the segment reconstruction area or the half reconstruction area, the system controlling unit 39 irradiates the subject P with strong X-rays at an electrocardiographic phase range specified by the operator and irradiating the subject P with weak X-rays (or stopping irradiation) at other electrocardiographic phase ranges. However, for example, an X-ray output can be changed depending on each area.

For example, when the imaging position is included within the segment reconstruction area or the half reconstruction area, the system controlling unit 39 controls the scan controlling unit 33 such that the X-ray output is greater than that when the imaging position is included within the no-electrocardiographic synchronization area. As a result, a clearer image can be obtained within an area requiring electrocardiographic synchronization.

After performing any of the above-described imaging operations, the system controlling unit 39 controls the scan controlling unit 33 to move the top plate 22 in the body axis direction by a predetermined distance and perform a next imaging. The system controlling unit 39 repeats the movement of the top plate 22 and imaging until the instruction to complete imaging is received from the operator.

In this way, the system controlling unit 39 confirms the type of area in which the imaging position is included. The system controlling unit 39 then sets whether electrocardiographic synchronized imaging is required and the type of reconstruction mode to be used based on the confirmed type of area. Therefore, optimal imaging conditions are automatically set for each region.

Figure 3:
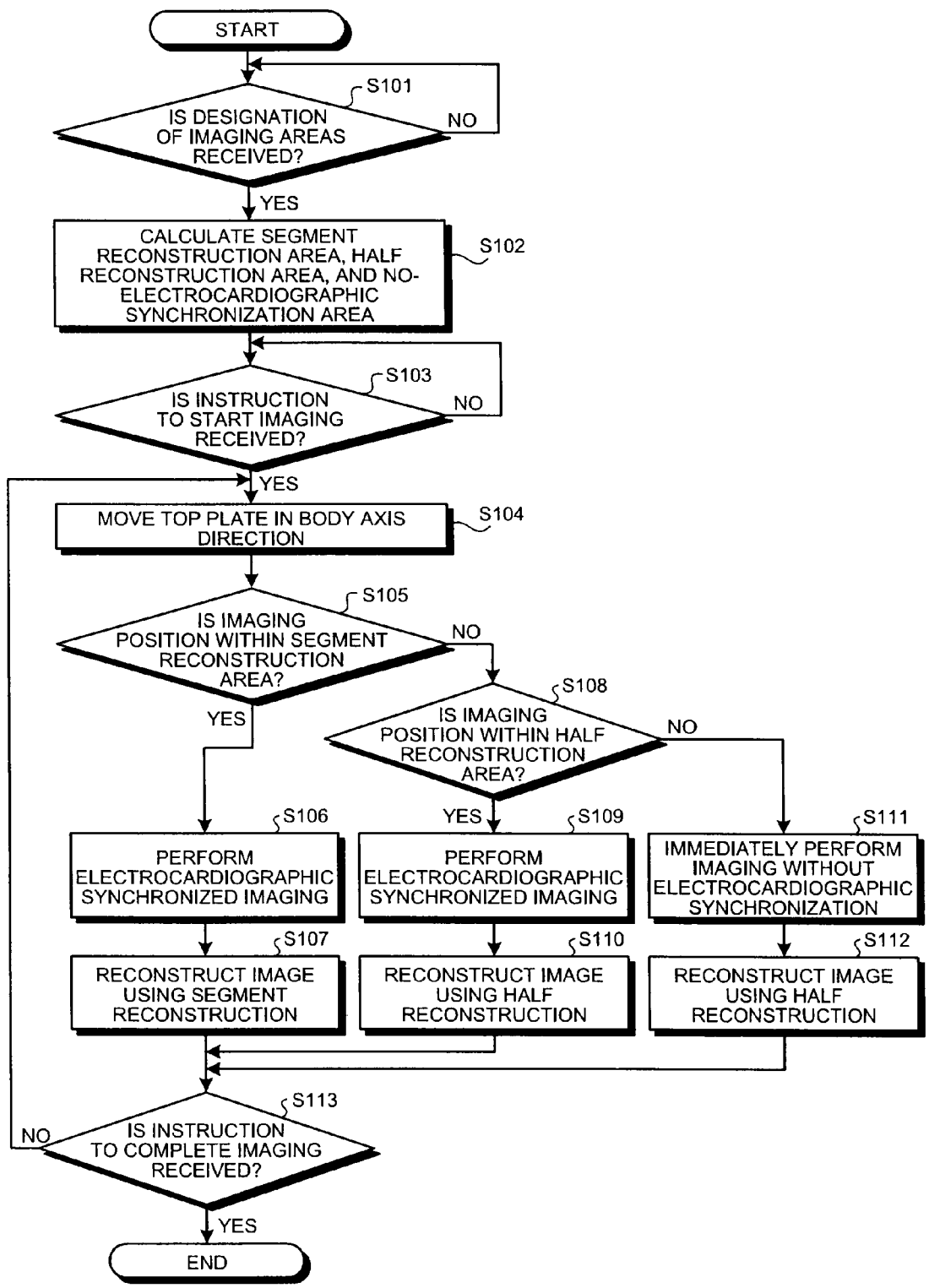
FIG. 3 is a flowchart of processes performed by the X-ray CT apparatus according to the first embodiment.

Next, processes performed by the X-ray CT apparatus 100 according to the first embodiment will be described. FIG. 3 is a flowchart of the processes performed by the X-ray CT apparatus 100 according to the first embodiment. As shown in FIG. 3, in the X-ray CT apparatus 100, when the console device 30 receives a designation of the imaging area from the operator (Yes at Step S101), the segment reconstruction area, the half reconstruction area, and the no-electrocardiographic synchronization area are respectively calculated based on the received designation (Step S102).

Then, when the console device 30 receives the instruction from the operator to start imaging (Yes at Step S103), the patient couch device 20 moves the top plate 22 in the body axial direction by a predetermined distance (Step S104).

Here, when the imaging position is included within the segment reconstruction area (Yes at Step S105), the gantry device 10 irradiates the subject P with the X-rays synchronously with the electrocardiographic waveforms and collects the projection data (Step S106). The console device 30 reconstructs the image from the projection data using segment reconstruction (Step S107).

When the imaging position is included within the half reconstruction area (No at Step S105 and Yes at Step S108), the gantry device 10 irradiates the subject P with the X-rays synchronously with the electrocardiographic waveforms and collects the projection data (Step S109). The console device 30 reconstructs the image from the projection data using half reconstruction (Step S110).

When the imaging position is included in the no-electrocardiographic synchronization area (No at Step S108), the gantry device 10 irradiates the subject with X-rays of a constant strength without synchronization with the electrocardiographic waveforms and collects the projection data (Step S111). The console device 30 reconstructs an image from the projection data using half reconstruction (Step S112).

The processes at Step S104 to S112 are then repeated until the console device 30 receives the instruction from the operator to complete imaging (No at Step S113). When the console device 30 receives the instruction to complete imaging (Yes at Step S113), imaging is completed.

As described above, according to the first embodiment, the system controlling unit 39 sets at least the imaging-subject area to be imaged and the heart imaging area included within the imaging-subject area and determined depending on the position and size of the heart on the subject P. When an image is taken, the system controlling unit 39 sets the imaging conditions for each region during imaging, based on each of the set areas. Therefore, when a wide area including the heart is imaged, the optimal imaging conditions are automatically set for each region, and the time required for the overall imaging operation can be shortened.

According to the first embodiment, when the system controlling unit 39 automatically calculates the half reconstruction area serving as the area surrounding the heart H, based on the heart imaging area designated by the operator, is described. However, the present invention is not limited thereto.

For example, the system controlling unit 39 can further receive a designation of an area that does not require a high temporal resolution in the image, namely an area having a small amount of movement in the region because of being away from the heart H. The system controlling unit 39 can then calculate the half reconstruction area based on the designation. An instance such as this will be described below according to a second embodiment. The newly received area is referred to, hereinafter, as a "heart periphery area".

Figure 4:
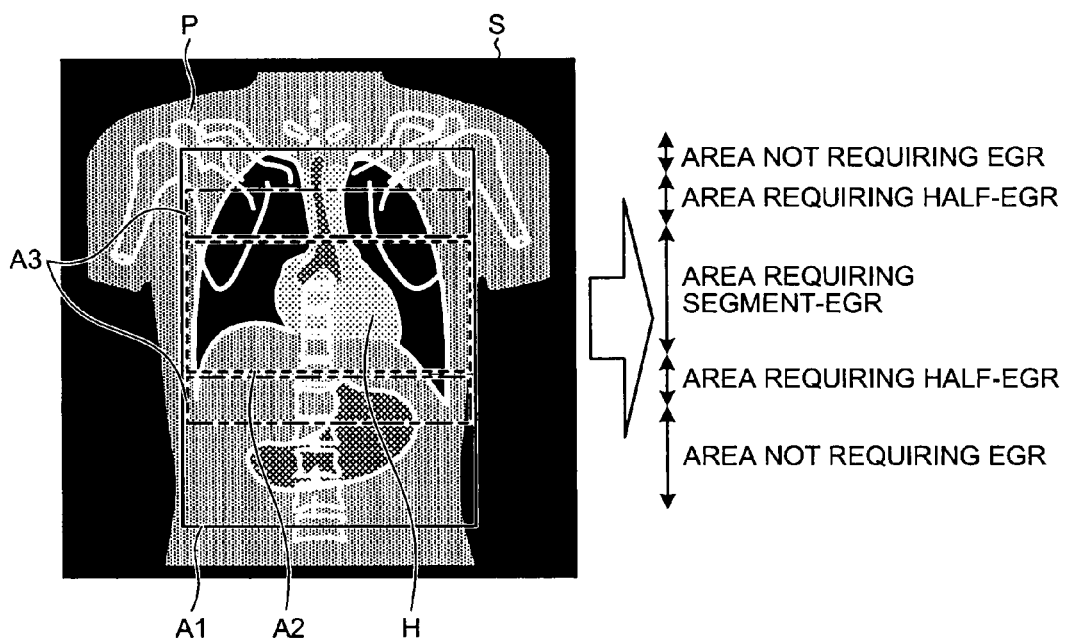
FIG. 4 is an explanatory diagram explaining a concept of an imaging condition setting method used in an X-ray CT apparatus according to a second embodiment.

FIG. 4 is an explanatory diagram explaining a concept of an imaging condition setting method used by the X-ray CT apparatus 100 according to the second embodiment. As shown in FIG. 4, in the X-ray CT apparatus 100 according to the second embodiment, the system controlling unit 39 receives designation of two heart periphery areas by, for example, displaying the frames A1 and A2 and receiving designations for the imaging-subject area and the heart imaging area, and displaying two frames A3 respectively positioned above and below the frame A2 and receiving the designation of the two heart periphery areas.

When the operator designates each imaging area, the system controlling unit 39 sets the heart imaging area (the area surrounded by the frame A2) as the "segment reconstruction area", the two heart periphery areas (two areas surrounded by the frames A3) as "half reconstruction areas", respectively, and the imaging-subject area (the area surrounded by the frame A1) from which the segment reconstruction area and the half reconstruction areas are excluded as the "no-electrocardiographic synchronization area". The system controlling unit 39 calculates the position and size of each area. The system controlling unit 39 also stores the calculated results in the imaging-area information storage unit 38 as the imaging area information.

In this way, according to the second embodiment, designation of areas that do not require a high temporal resolution in the image, namely areas having a small amount of movement in the region because of being away from the heart H, is further received. The half reconstruction areas are calculated based on the designation. Therefore, the operator can arbitrarily designate an imaging area in which an image having a high temporal resolution is required to be taken and an imaging area in which an image having a moderate temporal resolution is required to be taken, allowing the imaging conditions for each region to be set in more detail.

According to the first embodiment, a number of heartbeats used when the image is reconstructed using segment reconstruction is set in advance by the operator. However, the present invention is not limited thereto. For example, the system controlling unit 39 can further receive a specification of the number of heartbeats used when an image of the heart imaging area is reconstructed using segment reconstruction, in addition to the designation of the heart imaging area. An instance such as this will be described below according to a third embodiment.

Figure 5:
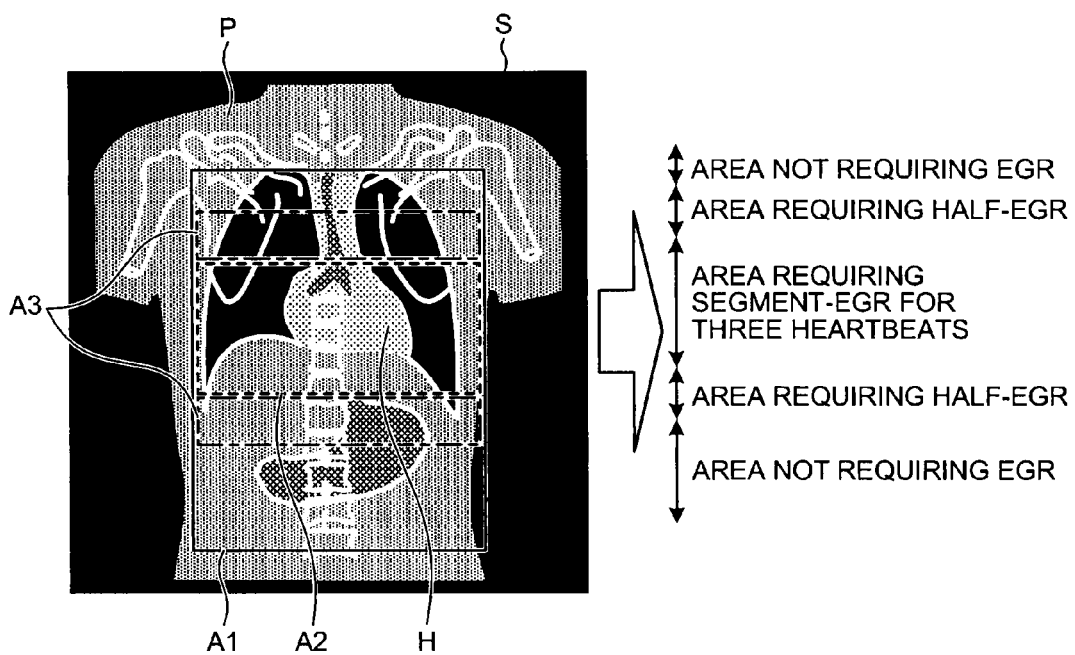
FIG. 5 is an explanatory diagram explaining a concept of an imaging condition setting method used by an X-ray CT apparatus according to a third embodiment.

FIG. 5 is an explanatory diagram explaining a concept of an image condition setting method used by the X-ray CT apparatus 100 according to the third embodiment. As shown in FIG. 5, in the X-ray CT apparatus 100 according to the third embodiment, the system controlling unit 39 displays the frames A1, A2, and A3 and receives designation of the imaging-subject area, the heart imaging area, and the heart periphery areas. The system controlling unit 39 also receives a specification of a number of heartbeats used when an image of the heart imaging area is reconstructed using segment reconstruction.

Here, it is assumed that the system controlling unit 39 receives three heartbeats as the number of heartbeats. In this case, when the system controlling unit 39 controls the image reconstruction processing unit 36, the system controlling unit 39 instructs the image reconstruction processing unit 36 to reconstruct the image using segment reconstruction from projection data collected over cardiac cycles of three heartbeats.

In this way, according to the third embodiment, the specification of the number of heartbeats used when the image of the heart imaging area is reconstructed using segment reconstruction is further received. As a result, the operator can arbitrarily specify a level of temporal resolution for the area in which an image having a high temporal resolution is required to be taken, allowing the imaging conditions for each region to be set in more detail.

According to the embodiments described above, when imaging is performed stepwisely using "step-and-shoot" is described. However, in "step-and-shoot", an imaging interval by which imaging is performed stepwisely is required to be set such that an area to be imaged is exhaustively imaged. Therefore, for example, when the designation of the imaging-subject area is received, the system controlling unit 39 can automatically calculate the imaging interval and set the imaging interval as an imaging condition. FIGS. 6A, 6B, 7 and 8 are explanatory diagrams explaining when the imaging interval is automatically set in "step-and-shoot".

In an X-ray CT apparatus including multiple rows of X-ray detectors, ordinarily, an imaging width in the body axis direction that can be imaged during a single imaging operation differs based on a field of view (FOV), even when imaging is performed at a same detector width. For example, as shown in FIG. 6B, compared to when the FOV is 30 centimeters, the imaging width in the body axis direction that can be imaged during a single imaging operation is wider when the FOV is 20 centimeters.

Therefore, when the system controlling area 39 displays the frame A1 and receives the designation of the imaging-subject area, the system controlling unit 39 sets the FOV based on a size of the imaging-subject area. Based on the set FOV, the system controlling unit 39 calculates the imaging width in the body axis direction that can be imaged during a single imaging operation. Then, based on a calculated result, the system controlling unit 39 sets individual imaging areas to be imaged by "step-and-shoot" in the imaging-subject area and displays frames indicating the set imaging areas.

Figure 6A:
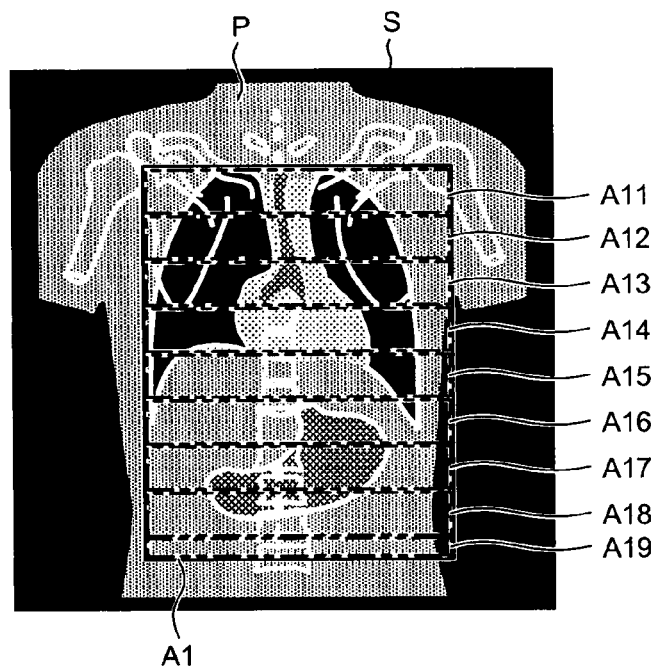
FIGS. 6A and 6B are explanatory diagrams explaining when an image interval is automatically set in "step-and-shoot"
Figure 6B:
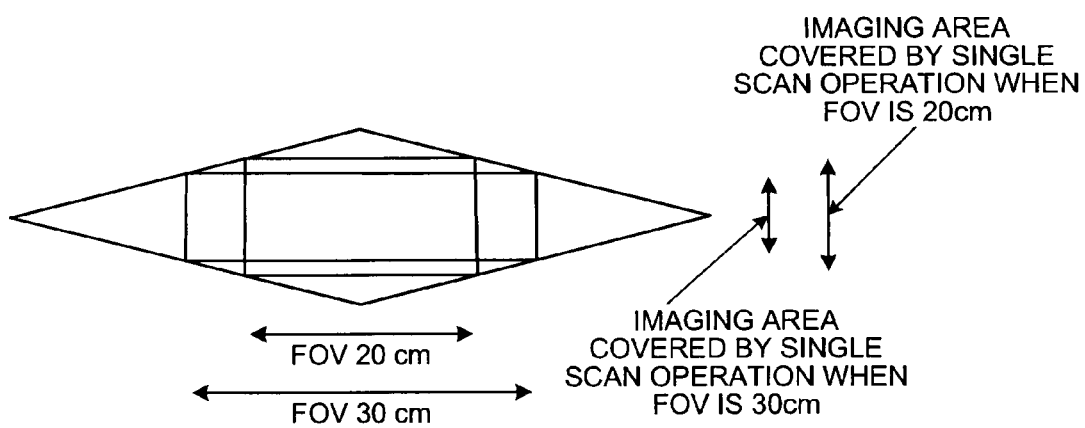

For example, as shown in FIG. 6A, the system controlling unit 39 sets the imaging areas having the calculated imaging width in the imaging-subject area (the area surrounded by the frame A1) such as to be aligned in sequence from one side (respective areas surrounded by frames A11 to A18). At this time, when an area remains that is not wide enough to have the calculated imaging width, the system controlling unit 39 sets only this area as an imaging area having a small imaging width (an area surrounded by frame A19).

Figure 7:
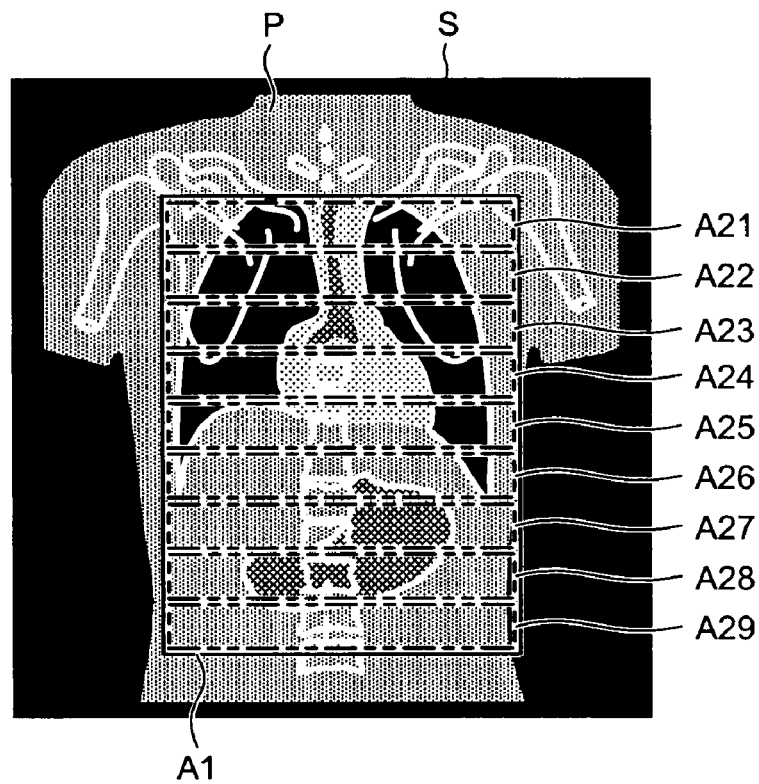
FIG. 7 is an explanatory diagram explaining when the image interval is automatically set in "step-and-shoot"

Alternatively, for example, as shown in FIG. 7, the system controlling unit 39 sets each imaging area without changing imaging frequency (a number of imaging areas set) from that of the example shown in FIG. 6A and by adjusting the imaging areas to have equal imaging widths in the body axis direction. The system controlling unit 39 then displays frames indicating the set imaging areas (areas surrounded by frames A21 to A29). In this case, image quality of each picked-up image is uniform.

After the individual imaging areas are set in the imaging-subject area in this way, the system controlling unit 39 sets the imaging width in the body axis direction for "step-and-shoot" such that the set imaging areas can be respectively imaged.

Figure 8:
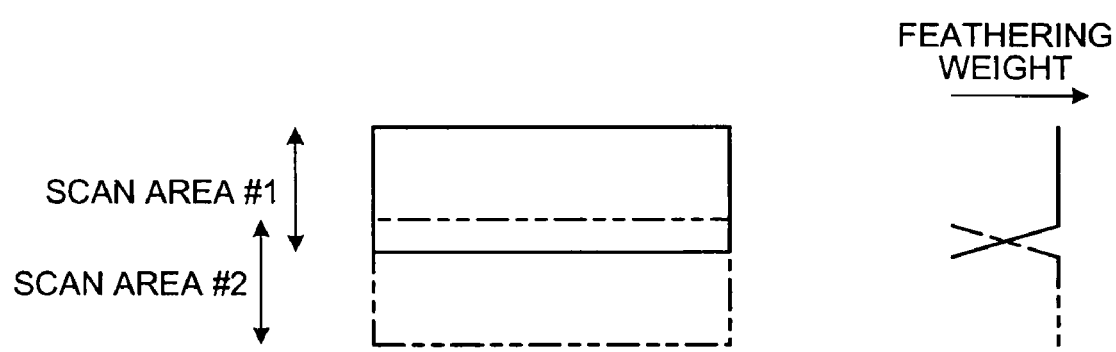
FIG. 8 is an explanatory diagram explaining when the image interval is automatically set in "step-and-shoot".

At this time, the system controlling unit 39 can set the imaging width for imaging by "step-and-shoot" under an assumption that connecting sections of the images taken at each imaging area are interpolated. For example, when an interpolation amount is two millimeters, as shown in FIG. 8, the imaging width in the body axis direction is set such that a two-millimeter overlap is ensured between adjacent imaging areas ("scan area #1" and "scan area #2" in FIG. 8). An interpolation operation assumed here can be trigonometric function, sigmoid, and the like, in addition to first-order interpolation such as that shown in FIG. 8 (interpolation performed using feathering weights). Alternatively, interpolation can be performed between individual images taken by electrocardiographic synchronized imaging, in addition to the individual images taken by "step-and-shoot".

According to the embodiments described above, when the image is reconstructed using segment reconstruction when an area including the heart is imaged and the image is reconstructed using half reconstruction when a periphery of the heart is imaged is described. However, when the periphery of the heart is imaged, the image can also be reconstructed using full reconstruction instead of half reconstruction. As a result, an image with higher image quality can be reconstructed.

According to the embodiments described above, when electrocardiographic synchronized imaging is performed is describe. However, the present invention is not limited thereto. The present invention can be similarly applied when, for example, respiration-synchronized imaging is performed. In this case, for example, the system controlling unit 39 receives a biological signal indicating a timing of respiration by a subject, inputted from a respiration detector or the like attached to the subject. The system controlling unit 39 controls the image reconstruction processing unit 36 and the scan controlling unit 33 based on the inputted biological signal.

As described above, the X-ray CT apparatus of the present invention is advantageous for imaging combining electrocardiographic synchronized imaging and "step-and-shoot". In particular, the X-ray CT apparatus is suitable for shortening the time required for the overall imaging operation.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. An X-ray CT apparatus comprising:
a top plate moving unit that stepwisely moves a top plate on which a subject is placed in a body axis direction;
a rotation mechanism unit that rotates an X-ray irradiating unit on a circular orbit approximately centering on the subject for every time the top plate moving unit moves the top plate;
a data collecting unit that collects projection data obtained by detecting X-rays passing through the subject;
an image reconstructing unit that reconstructs an image from the projection data collected by the data collecting unit; and
an imaging-area setting unit that sets, on the subject, a first imaging area including a first imaging region that moves cyclically or that moves non-cyclically, and a second imaging area including a second imaging region having less movement than the first imaging region, wherein
the imaging-area setting unit further sets, within the first imagining area, a third imaging area requiring an image having a predetermined temporal resolution and a fourth imaging area requiring an image having a better temporal resolution than the predetermined temporal resolution, and
the image reconstruction unit reconstructs a first image synchronously with movements of the first imaging region when the top plate moving unit moves the top plate to a position at which the first imaging area is irradiated with the X-rays, increases a frequency of synchronization during reconstructing the first image compared to when the top plate moving unit moves the top plate to a position at which the fourth imaging area is irradiated with the X-rays, when the top plate moving unit moves the top plate to a position at which the third imaging area is irradiated with the X-rays, and reconstructs a second image without synchronizing with movements of the second imaging region when the top plate moving unit moves the top plate to a position at which the second imaging area is irradiated with the X-rays.

2. The apparatus according to claim 1, wherein the image reconstructing unit reconstructs the image using full reconstruction mode when the top plate moving unit moves the top plate to the position at which the third imaging area is irradiated with the X-rays, and reconstructs the image using segment reconstruction mode when the fourth imaging area is irradiated with the X-rays.

3. The apparatus according to claim 1, wherein the image reconstructing unit reconstructs the image using full reconstruction mode when the top plate moving unit moves the top plate to the position at which the third imaging area is irradiated with the X-rays, and reconstructs the image using segment reconstruction mode when the fourth imaging area is irradiated with the X-rays.

4. The apparatus according to claim 1, further comprising a controlling unit that controls the X-ray irradiating unit such that output of the X-rays is increased when the top plate moving unit moves the top plate to the position at which the first imaging area is irradiated with the X-rays, compared to when the top plate moving unit moves the top plate to the position at which the second imaging area is irradiated with the X-rays.

5. The apparatus according to claim 1, further comprising a controlling unit that switches strength of the X-rays outputted from the X-ray irradiating unit synchronously with movement of the first imaging region, when the top plate moving unit moves the top plate to the position at which the first imaging area is irradiated with the X-rays.

6. The apparatus according to claim 1, further comprising a controlling unit that switches between the X-rays outputted from the X-ray irradiating unit being outputted and stopped synchronously with movements of the first imaging region, when the top plate moving unit moves the top plate to the position at which the first imaging area is irradiated with the X-rays.

7. The apparatus according to claim 1, further comprising:
a display unit that displays an image of the subject, wherein
the imaging-area setting unit sets the first imaging area and the second imaging area based on areas designated by an operator on the image of the subject displayed in the display unit.

8. The apparatus according to claim 1, further comprising:
a reference imaging-area setting unit that sets, on the subject, a fifth imaging area indicating an imaging area in the body axis direction and a sixth imaging area indicating an imaging area in a direction perpendicular to the body axis direction; and
an imaging area dividing unit that calculates an imaging width in the body axis direction that can be imaged by irradiation of the X-rays performed by the X-ray irradiating unit for every time the top plate is moved, based on the sixth imaging area set by the reference imaging-area setting unit, and divides the fifth imaging area into a plurality of areas adjacent to the body axis direction, based on the calculated imaging width, wherein
the top plate moving unit moves the top plate for each of the imaging areas into which the fifth imaging area is divided by the imaging area dividing unit.

9. The apparatus according to claim 8, wherein the imaging area dividing unit divides the fifth imaging area to allow the imaging areas after division respectively overlap with each other at adjacent sections by a predetermined width such that each image is provided with an overlapping section used to perform a predetermined interpolation operation on connecting sections, when a plurality of images reconstructed by the image reconstructing unit are connected.

* * * * *